(12) United States Patent
Bae et al.

(10) Patent No.: US 8,852,859 B2
(45) Date of Patent: Oct. 7, 2014

(54) METHOD AND/OR SYSTEM FOR MEASURING CONCENTRATION OF DETECTION TARGET USING TRANSMISSION OR REFLECTION OF LIGHT

(75) Inventors: Su-bong Bae, Suwon-si (KR); Chung-ung Kim, Yongin-si (KR); Ki-ju Lee, Suwon-si (KR); Jong-jin Park, Yongin-si (KR); Dong-hwi Cho, Suwon-si (KR); Jong-cheol Kim, Suwon-si (KR)

(73) Assignee: Samsung Electronics Co., Ltd., Suwon (KR)

( * ) Notice: Subject to any disclaimer, the term of this patent is extended or adjusted under 35 U.S.C. 154(b) by 1059 days.

(21) Appl. No.: 12/720,100

(22) Filed: Mar. 9, 2010

(65) Prior Publication Data

US 2010/0245565 A1    Sep. 30, 2010

(30) Foreign Application Priority Data

Mar. 31, 2009 (KR) ................ 10-2009-0027683

(51) Int. Cl.
*G01N 21/59* (2006.01)
*G01N 35/00* (2006.01)
*G01N 21/51* (2006.01)
*B01L 3/00* (2006.01)

(52) U.S. Cl.
CPC ............ *G01N 21/51* (2013.01); *B01L 3/5027* (2013.01); *G01N 21/59* (2013.01); *G01N 35/00069* (2013.01)
USPC ............................................. 435/4; 382/128

(58) Field of Classification Search
USPC ............................................. 382/128; 435/4
See application file for complete search history.

(56) References Cited

U.S. PATENT DOCUMENTS

| 5,126,569 | A | 6/1992 | Carlson |
| 6,144,444 | A | 11/2000 | Haworth et al. |
| 7,052,652 | B2 | 5/2006 | Zanzucchi et al. |
| 2002/0075471 | A1* | 6/2002 | Holec ............ 356/3.01 |
| 2003/0224457 | A1* | 12/2003 | Hurt et al. ......... 435/7.2 |
| 2009/0021741 | A1 | 1/2009 | Kim et al. |
| 2009/0221431 | A1* | 9/2009 | Yoo ................. 506/9 |
| 2009/0253130 | A1* | 10/2009 | Yoo ................. 435/6 |

FOREIGN PATENT DOCUMENTS

| KR | 10-0350022 | 8/2002 |
| WO | 2005/052598 A2 | 6/2005 |
| WO | WO 2005052598 A2 * | 6/2005 |
| WO | 2006/121266 A1 | 11/2006 |
| WO | 2007/001084 A1 | 1/2007 |

OTHER PUBLICATIONS

European Search Report dated Jun. 28, 2010 and issued in corresponding European Patent Application 10158096.7.

* cited by examiner

*Primary Examiner* — Sath V Perungavoor
*Assistant Examiner* — Jeffery Williams
(74) *Attorney, Agent, or Firm* — Staas & Haley LLP

(57) ABSTRACT

Provided are a method and/or apparatus for measuring the concentration of a detection target using the transmission or reflection of light. The system includes an illumination unit disposed over a biodisc and configured to apply light to the detection target included in the biodisc and a camera module disposed below the biodisc and configured to measure the amount of light transmitted through the detection target.

14 Claims, 21 Drawing Sheets

METHOD AND/OR SYSTEM FOR MEASURING CONCENTRATION OF DETECTION TARGET USING TRANSMISSION OR REFLECTION OF LIGHT

CROSS-REFERENCE TO RELATED APPLICATIONS

This application claims the benefit of Korean Patent Application No. 10-2009-0027683, filed on Mar. 31, 2009, in the Korean Intellectual Property Office, the disclosure of which is incorporated herein in its entirety by reference.

BACKGROUND OF THE INVENTION

The inventive concept relates to a method and/or system for measuring the concentration of a detection target using the transmission or reflection of light, and more particularly, to a method and system for measuring the concentration of a detection target using the transmission or reflection of light, by which the concentration of the detection target may be measured using the amount of light transmitted through or reflected by the detection target and quantitated.

A conventional system for measuring the concentration of a detection target disposed in a rotating biodisc is not a quantitative system but a qualitative system, so a user should confirm and determine an expression result with the naked eye. Accordingly, the user is highly likely to take a subject view of a detection result and reach a wrong conclusion.

Also, detection of an expression result using a conventional quantitative system involves designing a complicated optical system including a laser light source and a photodiode (PD) and detecting the expression result in a precise position. In this case, however, high detection reliability cannot be ensured, and designing the complicated optical system would be costly.

SUMMARY OF THE INVENTION

Additional aspects and/or advantages will be set forth in part in the description which follows and, in part, will be apparent from the description, or may be learned by practice of the invention.

The inventive concept provides a method and system for measuring the concentration of a detection target, by which the concentration of the detection target is reliably measured in a quantitative manner using a camera module and an illumination unit at low cost.

According to an aspect of the inventive concept, there is provided a system for measuring the concentration of a detection target using the transmission of light. The system includes: an illumination unit disposed over a biodisc and configured to apply light to the detection target included in the biodisc; and a camera module disposed below the biodisc and configured to measure the amount of light transmitted through the detection target.

The system may further include a printed circuit board (PCB) disposed below the biodisc. The camera module may be disposed on the PCB.

The system may further include a PCB disposed below the biodisc and having a hole. The camera module may be disposed below the hole of the PCB.

The system may further include a concentration determining unit configured to determine the concentration of the detection target based on the measured amount of light transmitted through the detection target.

A plurality of illumination units are arranged a predetermined distance apart from one another in a diametral direction of the biodisc. The camera module may move in the diametral direction of the biodisc and measures the concentration of the detection target disposed in a predetermined position.

The illumination unit may move in a diametral direction of the biodisc and apply light to the detection target disposed in a predetermined position. The camera module may move in the diametral direction of the biodisc and measure the concentration of the detection target disposed in the predetermined position.

According to another aspect of the inventive concept, there is provided a system for measuring the concentration of a detection target using the reflection of light. The system includes: an illumination unit disposed below a biodisc and configured to apply light to the detection target included in the biodisc; and a camera module disposed below the biodisc and configured to measure the amount of light reflected by the detection target.

The system may further include a PCB disposed below the biodisc. Each of the camera module and the illumination unit may be disposed on the PCB.

The system may further include a PCB disposed below the biodisc and having a hole. The illumination unit may be disposed on the PCB adjacent to the hole, and the camera module may be disposed below the hole of the PCB.

The system may further include: a first PCB disposed below the biodisc; and a second PCB spaced a predetermined distance apart from the first PCB over the first PCB and supported by a mechanism unit configured to support the illumination unit. The camera module may be disposed on the first PCB, and the illumination unit may be disposed on the second PCB.

The system may further include a concentration determining unit configured to determine the concentration of the detection target based on the measured amount of light reflected by the detection target.

The illumination unit may move in a diametral direction of the biodisc and apply light to the detection target disposed in a predetermined position. The camera module may move in the diametral direction of the biodisc and measure the concentration of the detection target disposed in the predetermined position.

According to another aspect there is provided a method of measuring the concentration of a detection target using the transmission or reflection of light. The method includes: applying light to the detection target included in a biodisc using a predetermined light source; measuring the amount of light transmitted through or reflected by the detection target included in the biodisc; and determining the concentration of the detection target based on the measured amount of light.

BRIEF DESCRIPTION OF THE DRAWINGS

The above features These and/or other aspects and advantages will become apparent and more readily appreciated from the following description of the embodiments taken in conjunction with the accompanying drawings in which.

Example embodiments will be more clearly understood from the following detailed description taken in conjunction with the accompanying drawings in which.

DETAILED DESCRIPTION OF THE PREFERRED EMBODIMENTS

Figure 1:
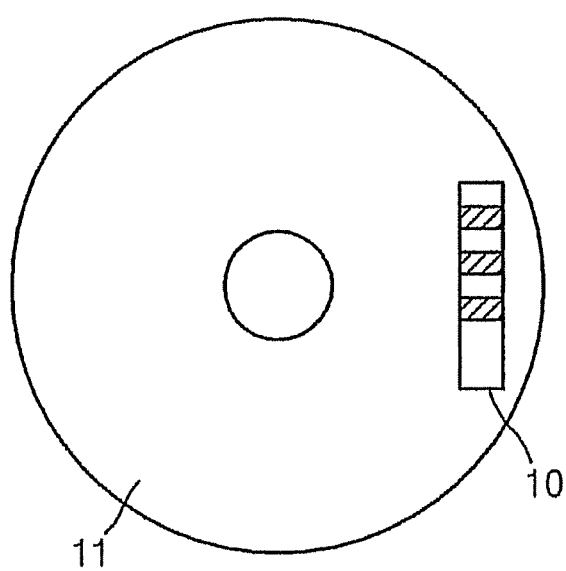
FIG. 1 is a plan view of a biodisc.

Reference will now be made in detail to the embodiments, examples of which are illustrated in the accompanying drawings, wherein like reference numerals refer to the like elements throughout. The embodiments are described below to explain the present invention by referring to the figures.

Hereinafter, the present inventive concept will be described in detail by explaining example embodiments with reference to the attached drawings. Like reference numerals in the drawings denote like elements.

FIG. 1 is a plan view of a biodisc.

Referring to FIG. 1, a detection target 10 may be included in the biodisc 11. The embodiment provides a system for measuring the concentration of the detection target 10 included in the biodisc 11.

The concentration of the detection target 10 may be measured using two methods. First, the amount of light transmitted through the detection target 10 may be measured. Second, the amount of light reflected by the detection target 10 may be measured.

Figure 2A:
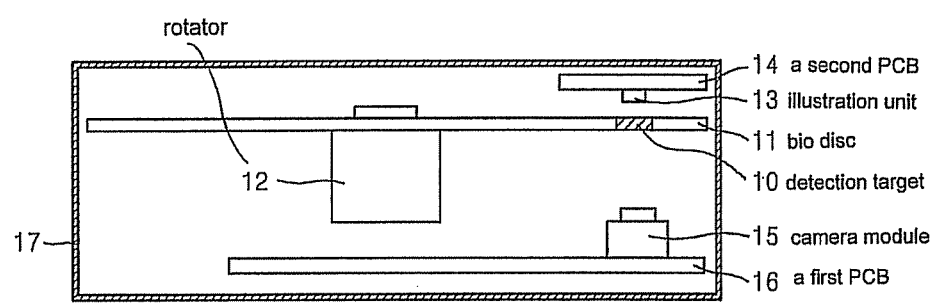
FIG. 2A is a diagram of a system for measuring the concentration of a detection target using the transmission of light according to an example embodiment.
Figure 3A:
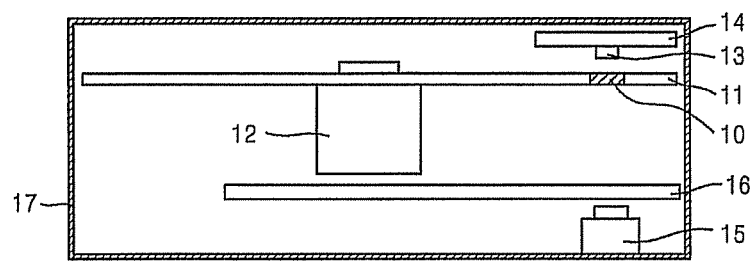
FIG. 3A is a diagram of a system for measuring the concentration of a detection target using the transmission of light according to another example embodiment.
Figure 4A:
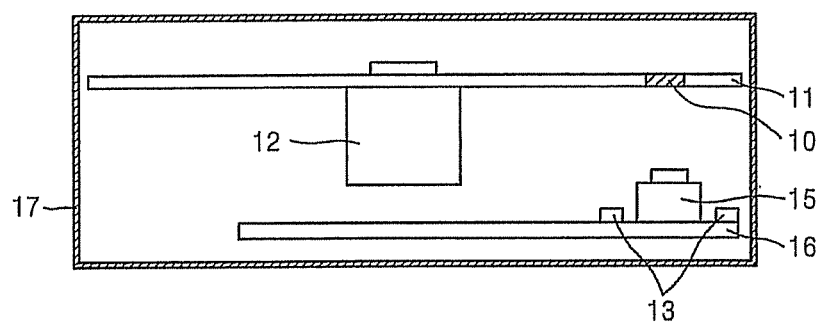
FIG. 4A is a diagram of a system for measuring the concentration of a detection target using the reflection of light according to an example embodiment.
Figure 5A:
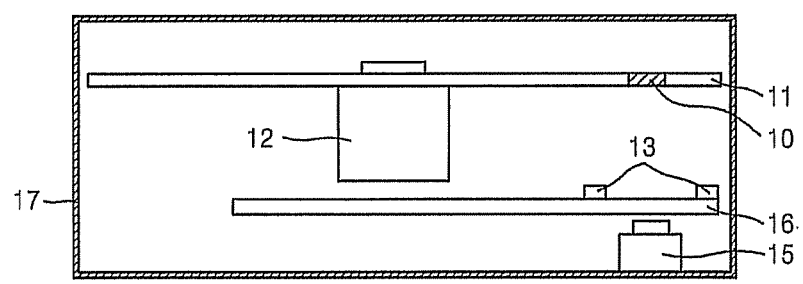
FIG. 5A is a diagram of a system for measuring the concentration of a detection target using the reflection of light according to another example embodiment.
Figure 6A:
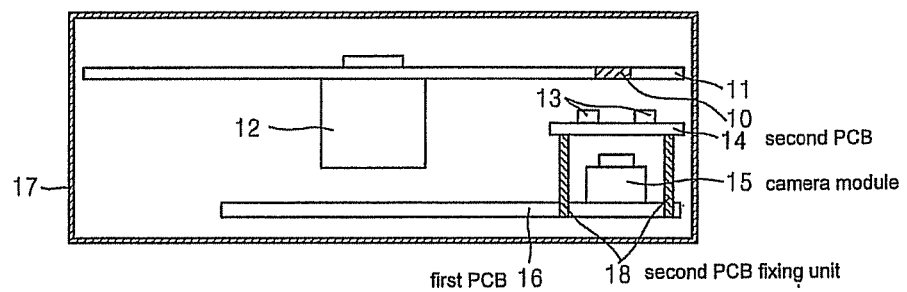
FIG. 6A is a diagram of a system for measuring the concentration of a detection target using the reflection of light according to another example embodiment.

FIGS. 2A and 3A are diagrams of systems for measuring the concentration of a detection target using the transmission of light according to example embodiments, and FIGS. 4A, 5A, and 6A are diagrams of systems for measuring the concentration of a detection target using the reflection of light according to example embodiments. Hereinafter, the systems for measuring the concentration of the detection target according to various example embodiments will be described in more detail with reference to the drawings.

Figure 2B:
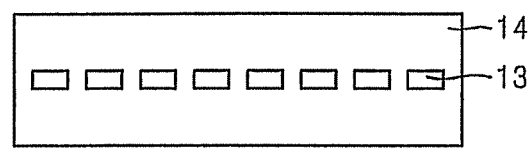
FIG. 2B is a diagram of an illumination unit of the system of FIG. 2A, which is disposed in a second printed circuit board (PCB), according to an example embodiment.

FIG. 2A is a diagram of a system for measuring the concentration of a detection target using the transmission of light according to an example embodiment, and FIG. 2B is a diagram of an illumination unit of the system of FIG. 2A, which is disposed in a second printed circuit board (PCB), according to an example embodiment.

Referring to FIG. 2A, to measure the concentration of a detection target 10 included in a biodisc 11 that rotates by a rotator 12, a second PCB 14 may be located over the biodisc 11, and an illumination unit 13 may be located under the second PCB 14 and apply light to the detection target 10 included in the biodisc 11.

A camera module 15 may be located below the biodisc 11 and measure the transmission of light applied by the illumination unit 13 to the detection target 10. Also, a concentration determining unit (not shown) may be further provided to determine the concentration of the detection target 10 based on the measured transmission of light. Various apparatuses, such as a central processing unit (CPU) or a microcontroller, may be used as the concentration determining unit.

Meanwhile, FIG. 2A illustrates a case where the camera module 15 is located on a top surface of a first PCB 16 disposed below the biodisc 11.

The camera module 15 may use a high-performance photographing method to measure the concentration of the detection target 10 that is rotating. A complementary metal oxide semiconductor (CMOS) camera or a charge-coupled device (CCD) camera may be used as the camera module 15. However, the present inventive concept is not limited thereto and various camera modules may be adopted.

Meanwhile, the illumination unit 13 according to the present inventive concept may be a light emitting diode (LED) array or a backlight unit. Alternatively, a light source, such as a cold cathode fluorescent lamp (CCFL), or an additional light emitting unit, such as a xenon flash, may be used as the illumination unit 13.

FIG. 2B illustrates where the illumination unit 13 formed on the second PCB 14 of FIG. 2A is an LED array. As illustrated in FIG. 2B, the LED array may include at least two LEDs arranged in a series according to an embodiment.

In another case, the illumination unit 13 may be a backlight unit, which is a light source of a liquid crystal display (LCD) that is a nonemissive display device. Typically, a CCFL is most widely used as the backlight unit. When the backlight unit is used as the illumination unit 13, detection sensitivity may be degraded, but a uniform illumination condition may be provided, as compared with when an LED array is used as the illumination unit 13 according to another embodiment.

As described above, a quantitative system for measuring the concentration of a detection target using the transmission of light may improve a detection limitation at a low concentration and increase a variation of a measured signal with respect to the concentration of the detection target 10, thereby enhancing the sensitivity of the system to the concentration of the detection target 10.

Figure 3B:
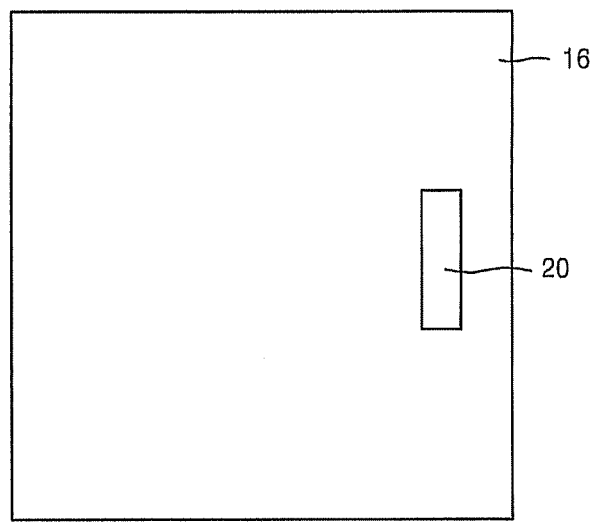
FIG. 3B is a diagram of an illumination unit of the system of FIG. 3A, which is disposed in a first PCB, according to an example embodiment.

FIG. 3A is a diagram of a system for measuring the concentration of a detection target using the transmission of light according to another embodiment, and FIG. 3B is a diagram of an illumination unit of the system of FIG. 3A, which is disposed in a first PCB, according to an example embodiment.

Referring to FIG. 3A, unlike the system of FIG. 2A in which the camera module 15 is disposed on the top surface of the first PCB 16, a camera module 15 may be located on a case 17 below a first PCB 16. As illustrated in FIG. 3B, since the first PCB 16 is located between the camera module 15 and a detection target 10 to be photographed, a hole 20 may be formed in the first PCB 16 in consideration of a view angle of the camera module 15.

In the system of FIGS. 3A and 3B, light irradiated by an LED array may be transmitted through the detection target 10 and incident to the camera module 15, thereby improving the detection sensitivity of the system to the concentration of the detection target 10. That is, the system of FIG. 3A may improve a detection limitation at a low concentration and increase detection sensitivity, which is a variation of a measured signal with respect to the concentration of the detection target 10.

Figure 4B:
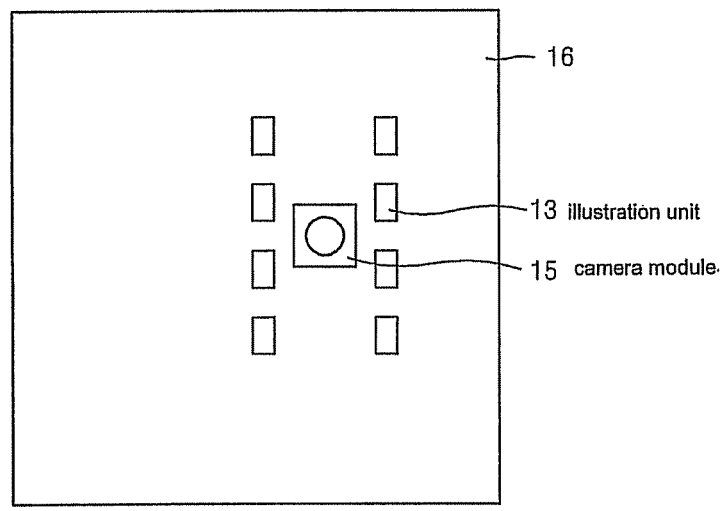
FIGS. 4B and 4C are diagrams of an illumination unit and camera module of the system of FIG. 4A, which are disposed in a first PCB, according to an example embodiment.
Figure 4C:
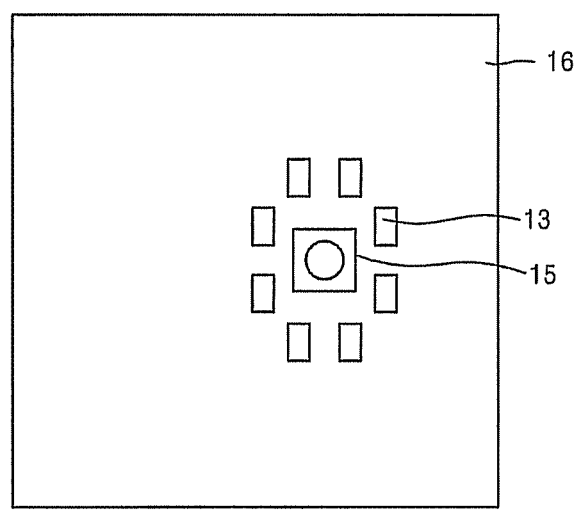

FIG. 4A is a diagram of a system for measuring the concentration of a detection target using the reflection of light according to an embodiment, and FIGS. 4B and 4C are diagrams of an illumination unit and camera module of the system of FIG. 4A, which are disposed in a first PCB, according to an example embodiment.

Unlike the systems of FIGS. 2A and 3A, in the system of FIG. 4A, since an illumination unit 13 and a camera module 15 are disposed in the same direction, the camera module 15 may measure not the transmission of light but the reflection of light. As illustrated in FIG. 4A, the illumination unit 13 may be disposed below a biodisc 11 and apply light to a detection target 10 included in the biodisc 11. Also, the camera module 15 may be disposed below the biodisc 11 and measure the reflection of light applied by the illumination unit 13 to the detection target 10.

Also, a concentration determining unit (not shown) may be further provided to determine the concentration of the detection target 10 based on the measured reflection of light. Various apparatuses, such as a CPU or a microcontroller, may be used as the concentration determining unit.

Meanwhile, each of the camera module 15 and the illumination unit 13 may be disposed on a top surface of a first PCB 16. Referring to FIGS. 4B and 4C, the camera module 15 may be disposed on the top surface of the first PCB 16 and surrounded by the illumination unit 13, which is an LED array. As described above, the illumination unit 13 is not limited to the LED array. Also, even if the illumination unit 13 is the LED array, arrangement of LEDs is not limited to FIGS. 4B and 4C and may be variously changed.

Figure 5B:
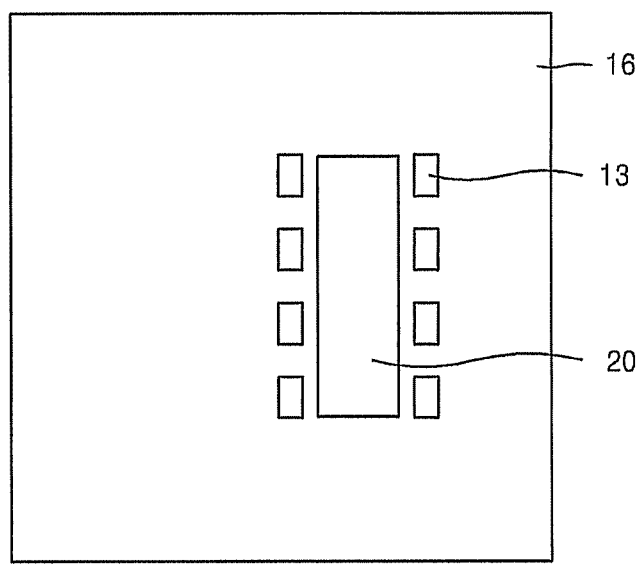
FIGS. 5B and 5C are diagrams of an illumination unit of the system of FIG. 5A, which are disposed in a first PCB, according to an example embodiment.
Figure 5C:
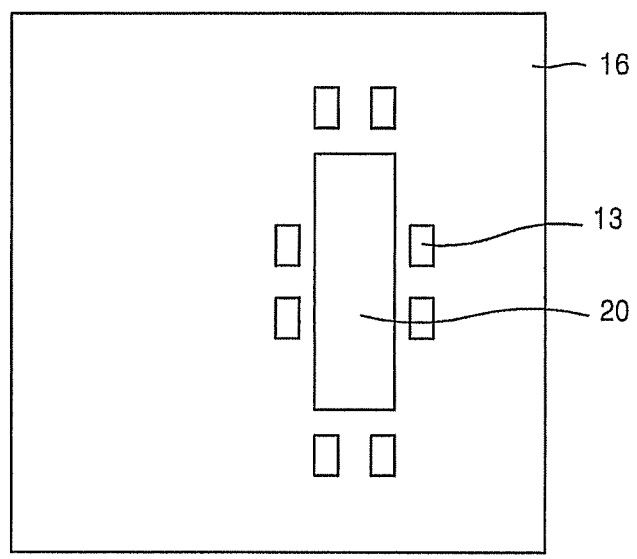

FIG. 5A is a diagram of a system for measuring the concentration of a detection target using the reflection of light according to another embodiment, and FIGS. 5B and 5C are diagrams of an illumination unit of the system of FIG. 5A, which are disposed in a first PCB, according to an example embodiment.

Referring to FIG. 5A, unlike the system of FIG. 4A in which the camera module 15 is disposed on the top surface of the first PCB 16, a camera module 15 may be located on a case 17 below a first PCB 16. As illustrated in FIGS. 5B and 5C, since the first PCB 16 is located between the camera module 15 and a detection target 10 to be photographed, a hole 20 may be formed in the first PCB 16 in consideration of a view angle of the camera module 15. The size of the hole 20 formed in the first PCB 16 may be variously changed according to a designer's selection.

Also, FIGS. 5B and 5C illustrate a case where an LED array functioning as the illumination unit 13 is formed on the first PCB 16. However, the illumination unit 13 is not limited to the LED array. Also, even if the illumination unit 13 is the LED array, arrangement of LEDs is not limited to FIGS. 5B and 5C and may be variously changed.

Figure 6B:
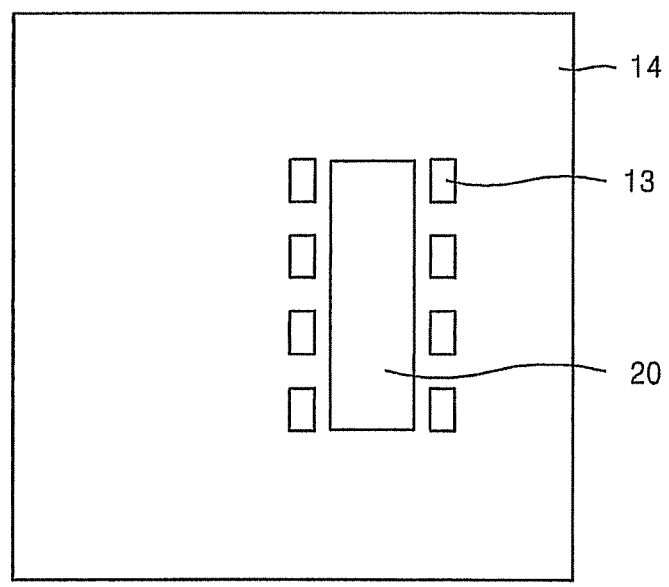
FIGS. 6B and 6C are diagrams of an illumination unit of the system of FIG. 6A, which are disposed in a second PCB, according to an example embodiment.
Figure 6C:
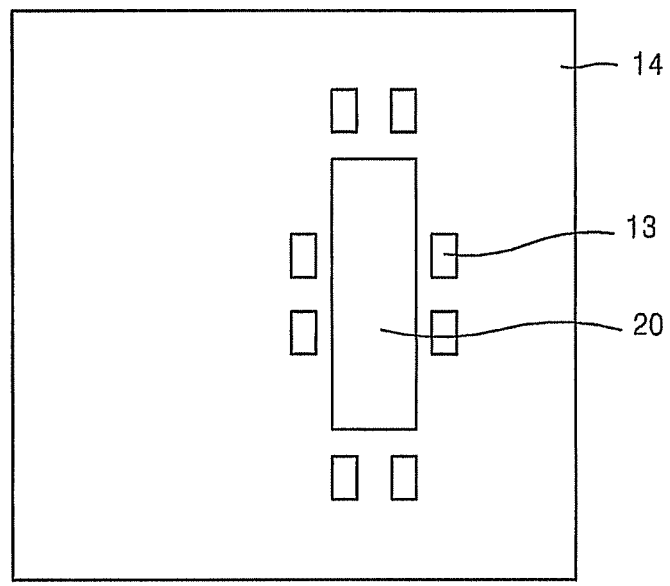

FIG. 6A is a diagram of a system for measuring the concentration of a detection target using the reflection of light according to another example embodiment, and FIGS. 6B and 6C are diagrams of an illumination unit of the system of FIG. 6A, which are disposed in a second PCB, according to an example embodiment.

Referring to FIG. 6A, a camera module 15 may be disposed on a top surface of a first PCB 16, and an illumination unit 13 may be disposed on a top surface of a second PCB 14 that may be spaced a predetermined distance apart from the first PCB 16 over and parallel to the first PCB 16. The second PCB 14 may be supported by second-PCB fixing unit 18.

Meanwhile, as illustrated in FIGS. 6B and 6C, since the second PCB 14 is located between the camera module 15 and the detection target 10 to be photographed, a hole 20 may be formed in the second PCB 14 in consideration of a view angle of the camera module 15. The size of the hole 20 formed in the second PCB 14 may be variously changed according to a designer's selection.

Also, FIGS. 6B and 6C illustrate a case where an LED array functioning as the illumination unit 13 is formed on the second PCB 14. However, the illumination unit 13 is not limited to the LED array. Also, even if the illumination unit 13 is the LED array, arrangement of LEDs is not limited to FIGS. 5B and 5C and may be variously changed.

Figure 7:
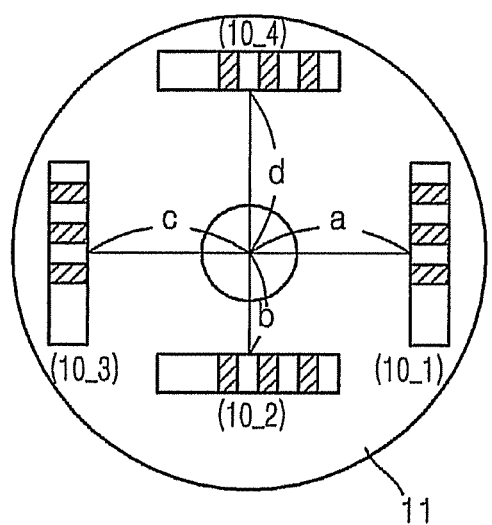
FIG. 7 is a cross-sectional view of a biodisc in which a plurality of detection targets are disposed in different positions.

FIG. 7 is a cross-sectional view of a biodisc in which a plurality of detection targets are disposed in different positions.

A plurality of detection targets may be disposed in different positions in a biodisc 11. Specifically, a first detection target 10_1 may be disposed a distance of radius "a" from the center of the biodisc 11, a second detection target 10_2 may be disposed a distance of radius "b" from the center of the biodisc 11, a third detection target 10_3 may be disposed a distance of radius "c" from the center of the biodisc 11, and a fourth detection target 10_4 may be disposed a distance of radius "d" from the center of the biodisc 11.

When the plurality of detection targets 10_1, 10_2, 10_3, and 10_4 are disposed in the single biodisc 11, a camera module or an illumination unit may be moved in a diametral direction of the biodisc 11. In other words, the camera module or the illumination unit may be freely moved to specific positions of the biodisc 11 where the detection targets 10_1, 10_2, 10_3, and 10_4 are located.

Figure 8A:
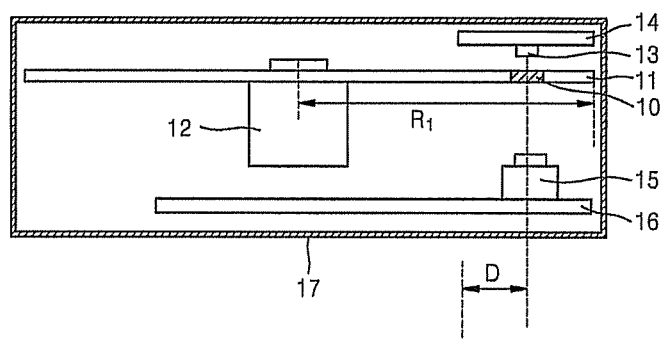
FIG. 8A and FIG. 8B illustrates the reason that positions of a camera module and an illumination unit should be changed according to the size of a biodisc.
Figure 8B:
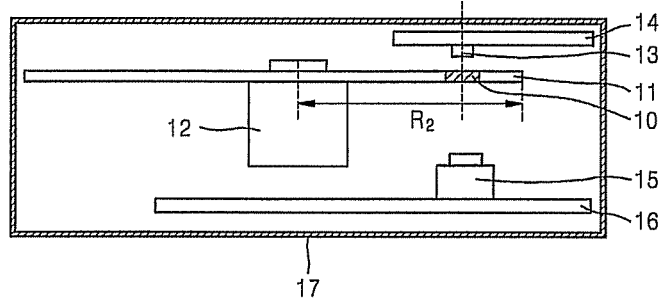

FIG. 8A and FIG. 8B illustrate that positions of a camera module and an illumination unit should be changed according to the size of a biodisc.

In FIG. 8A shows where a biodisc 11 has a radius of R1, and FIG. 8B shows a case where a biodisc 11 has a radius of R2 smaller than the radius of R1. When the radius of the biodisc 11 is reduced, a position of a detection target 10 is changed by a distance D. Thus, when a camera module 15 and an illumination unit 13 used in FIG. 8A are intended to be used in FIG. 8B, the camera module 15 and the illumination unit 13 need to be moved by the distance of D toward the center of the biodisc 11.

For this reason, a system for measuring the concentration of a detection target using the transmission or reflection of light, which is designed to be capable of moving a camera module and/or an illumination unit, is provided.

Figure 9A:
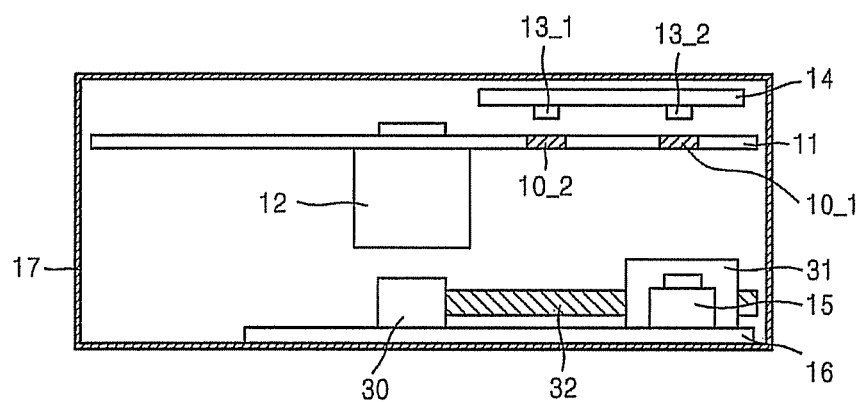
FIG. 9A is a diagram of a system for measuring the concentration of a detection target using the transmission of light, in which a camera module is movably mounted, according to an example embodiment.
Figure 9B:
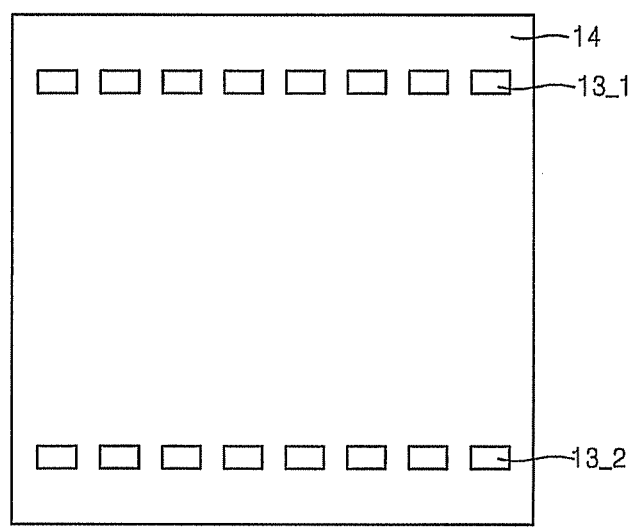
FIG. 9B is a diagram of an illumination unit of the system of FIG. 9A, which is disposed in a second PCB, according to an example embodiment.

FIG. 9A is a diagram of a system for measuring the concentration of a detection target using a transmission of light, in which a camera module is movably mounted, according to an embodiment, and FIG. 9B is a diagram of an illumination unit of the system of FIG. 9A, which is disposed in a second PCB, according to an embodiment;

Referring to FIG. 9A, a camera module 15 may be disposed below a biodisc 11 and measure the transmissions of light applied by first and second illumination units 13_1 and 13_2 to detection targets 10_1 and 10_2. The camera module 15 may move in a diametral direction of the biodisc 11 and measure the concentration of the first detection target 10_1 or the second detection target 10_2 located in a predetermined position.

To move the camera module 15 in the diametral direction of the biodisc 11, the system for measuring the concentration of the detection target using the transmission of light according to the embodiment may further include a feeding system, which includes a feeding motor 30, a mechanism unit 31, and a support unit 32.

The mechanism unit 31 may fix the camera module 15. The mechanism unit 31 may be connected to the support unit 32 and designed to slide in the diametral direction of the biodisc 11. Meanwhile, the feeding motor 30 may supply power to allow the mechanism unit 31 to move according to the size of the biodisc 11 or the position of the first detection target 10_1 or second detection target 10_2 to be photographed.

When the system for measuring the concentration of a detection target using the transmission of light according to the embodiment includes the feeding system as described above, even if the size of the biodisc 11 is reduced or the position of the detection target 10_1 or 10_2 is changed, the concentration of the detection target 10_1 or 10_2 may be measured by moving the camera module 15 to a desired position instead of re-designing the system.

The first and second illumination units 13_1 and 13_2 are formed on a bottom surface of a second PCB 14 disposed over the biodisc 11. Two illumination units 13_1 and 13_2 or more may be arranged a predetermined distance apart from one another in the diametral direction of the biodisc 11.

In the embodiment, since the first and second illumination units 13_1 and 13_2 are not structured to move in the diametral direction of the biodisc 11, the first and second illumination units 13_1 and 13_2 should be arranged in consideration of the size of the biodisc 11 or the position of the detection target 10_1 or 10_2. Referring to FIG. 9A, although the camera module 15 is capable of moving in the diametral direction of the biodisc 11 by the feeding motor 30, the first and second illumination units 13_1 and 13_2 are fixed on the bottom surface of the second PCB 14. Accordingly, a plurality of illumination units 13_1 and 13_2 may be provided on the bottom surface of the second PCB 14.

Specifically, the two illumination units 13_1 and 13_2 may be arranged on the bottom surface of the second PCB 14 such that the first illumination unit 13_1 is used to measure the concentration of the first detection target 10_1, while the second illumination unit 13_2 is used to measure the concentration of the second detection target 10_2.

FIG. 9B illustrates where each of the first and second illumination unit 13_1 and 13_2 formed on the second PCB 14 of FIG. 9A is an LED array according to an embodiment. As illustrated in FIG. 9B, two LED arrays may be sequentially arranged. However, three or more LED arrays may be sequentially arranged.

Figure 10:
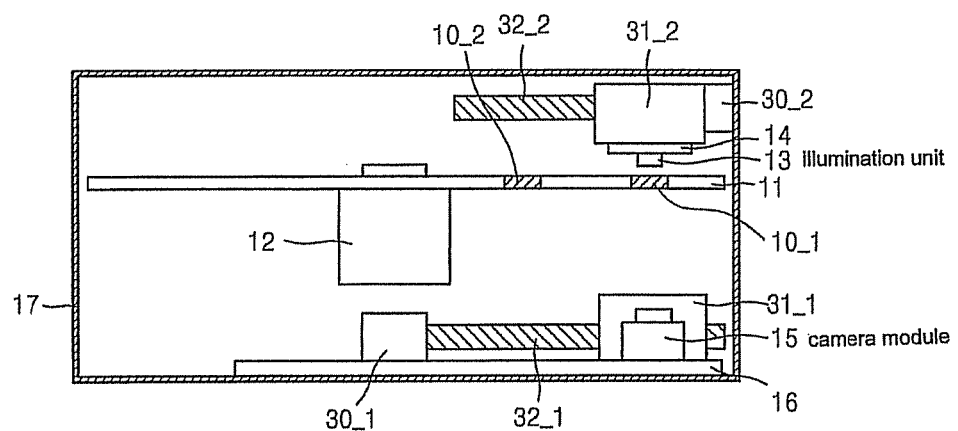
FIG. 10 is a diagram of a system for measuring the concentration of a detection target using the transmission of light, in which a camera module and an illumination unit are mounted to be capable of moving separately, according to an example embodiment.

FIG. 10 is a diagram of a system for measuring the concentration of a detection target using the transmission of light, in which a camera module and an illumination unit are mounted to be capable of moving separately, according to an example embodiment.

Unlike the system of FIG. 9A in which each of the first and second illumination units 13_1 and 13_2 is fixed, in the system of FIG. 10, an illumination unit 13 may be designed to move in a diametral direction of a biodisc like a camera module 15 and apply light to a detection target disposed in a predetermined position.

Like in FIG. 9A, the system for measuring the concentration of the detection target using the transmission of light according to the embodiment may further include a first feeding system, which includes a first feeding motor 30_1, a first mechanism unit 31_1, and a first support unit 32_1 to move the camera module 15 in the diametral direction of the biodisc 11.

In addition, the system according to the embodiment may further include a second feeding system, which includes a second feeding motor 30_2, a second mechanism unit 31_2, and a second support unit 32_2 to move the illumination unit 13 in the diametral direction of the biodisc 11.

The illumination unit 13 may be fixed on the second mechanism 31_2. The second mechanism unit 31_2 may be connected to the second support unit 32_2 and designed to slide in the diametral direction of the biodisc 11. Meanwhile, the second mechanism unit 31_2 may receive power from the second feeding motor 30_2 and move to a position of a first detection target 10_1 or second detection target 10_2 to be photographed. Thus, the illumination unit 13 may move in the diametral direction of the biodisc 11 and apply light to the detection target 10_1 or 10_2 disposed in a predetermined position.

When a feeding system is applied not only to the camera module 15 but also to the illumination unit 13 as in the embodiment, even if the size of the biodisc 11 is reduced or the position of the detection target 10_1 or 10_2 is changed, the concentration of the detection target 10_1 or 10_2 may be measured by moving the camera module 15 to a predetermined position instead of re-designing the system.

Figure 11:
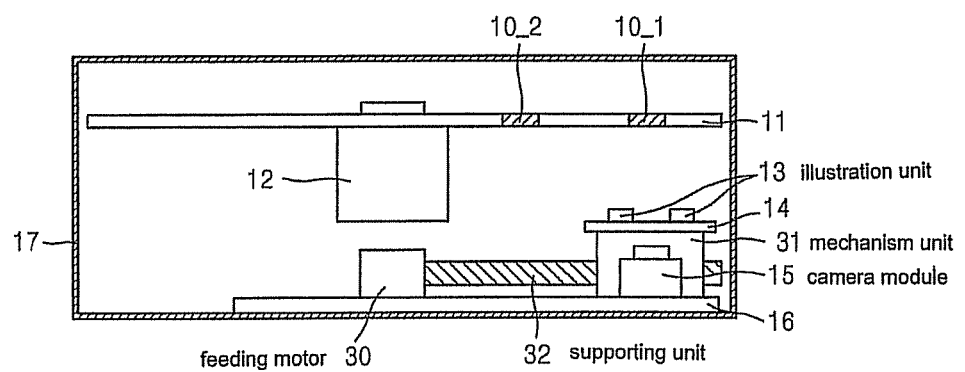
FIG. 11 is a diagram of a system for measuring the concentration of a detection target using the reflection of light, in which a camera module and an illumination unit are mounted to be capable of moving together, according to an example embodiment.

FIG. 11 is a diagram of a system for measuring the concentration of a detection target using the reflection of light, in which a camera module and an illumination unit are mounted to be capable of moving simultaneously, according to an embodiment.

Referring to FIG. 11, a camera module 15 and an illumination unit 13 may be disposed below a biodisc 11, and the camera module 15 may measure the reflection of light applied by the illumination unit 13 to a first detection target 10_1 or a second detection target 10_2. The camera module 15 and the illumination unit 13 may move in a diametral direction of the biodisc 11 and measure the concentration of the first detection target 10_1 or second detection target 10_2 disposed in a predetermined position.

To move the camera module 15 in the diametral direction of the biodisc 11, the system for measuring the concentration of the detection target using the reflection of light according to the embodiment may further include a feeding system, which includes a feeding motor 30, a mechanism unit 31, and a support unit 32.

Since the feeding motor 30, the mechanism unit 31, and the support unit 32 are the same as in the embodiment described with reference to FIG. 9A, a detailed description thereof will be omitted.

Meanwhile, the illumination unit 13 may be arranged on a top surface of a second PCB 14 formed on a top surface of the mechanism unit 31 that fixes the camera module 15. The arrangement of the illumination unit 13 on the second PCB 14 according to the embodiment is the same as in the embodiment described with reference to FIGS. 6B and 6C.

In conclusion, since the illumination unit 13 and the camera module 15 are capable of moving to a specific position using a single feeding system, the design of the system for measuring the concentration of a detection target using the reflection of light is very simple, thus reducing a time and cost required to design the system.

Figure 12:
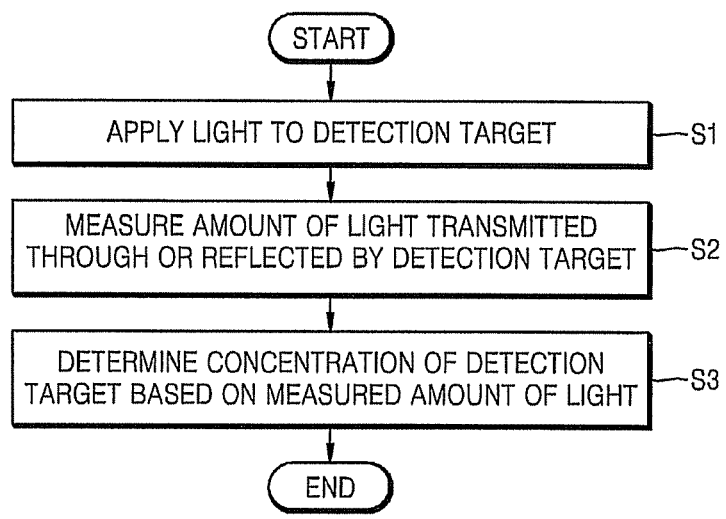
FIG. 12 is a flowchart illustrating a method of measuring the concentration of a detection target using the transmission or reflection of light according to an example embodiment.

FIG. 12 is a flowchart illustrating a method of measuring the concentration of a detection target using the transmission or reflection of light according to an embodiment.

Referring to FIG. 12, a method of measuring the concentration of the detection target 10 using the transmission or reflection of light may include applying light to the detection target 10 using a light source, such as the illumination unit 13, in operation S1. Thereafter, the camera module 15 may measure the amount of light transmitted through or reflected by the detection target 10, in operation S2. In operation S3, the concentration of the detection target 10 may be determined based on the measured amount of light transmitted through or reflected by the detection target 10.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A system for measuring a concentration of a detection target using the transmission of light, the system comprising:
    an illumination unit disposed over a biodisc and configured to apply light to the detection target included in the biodisc;
    a camera module disposed below the biodisc and configured to measure an amount of the light applied by the illumination unit that is transmitted through the detection target;
    a concentration determining unit configured to determine the concentration of the detection target based on the measured amount of the light transmitted through the detection target; and
    a first feeding system having a first feeding motor to move the camera module in a diametral direction of the biodisc.

2. The system of claim 1, further comprising a printed circuit board (PCB) disposed below the biodisc,
    wherein the camera module is disposed on the PCB.

3. The system of claim 1, further comprising a PCB having a hole disposed below the biodisc,
    wherein the camera module is disposed below the hole of the PCB.

4. The system of claim 1, wherein a plurality of illumination units are arranged a predetermined distance apart from one another in a diametral direction of the biodisc, and wherein a first illumination unit is used to measure the concentration of the detection target and a second illumination unit is used to measure a concentration of a second detection target.

5. The system of claim 1, wherein the illumination unit moves in a diametral direction of the biodisc and applies the light to the detection target disposed in a predetermined position,
    wherein the camera module moves in the diametral direction of the biodisc and measures the concentration of the detection target disposed in the predetermined position.

6. The system of claim 2, wherein the illumination unit and the camera module unit move separately relative to the PCB.

7. The system of claim 1, further comprising:
    a second feeding system having a second feeding motor, a second mechanism, a second supporting unit to move the illumination unit to move in a diametral direction of the biodisc and to move separately from the camera module.

8. The system of claim 4, the camera module moves in the diamentral direction of the biodisc and measures the concentration of the detection target disposed in a predetermined position.

9. A method of measuring a concentration of a detection target using the transmission or reflection of light, the method comprising:
    applying light to the detection target in a biodisc using a predetermined light source;
    measuring an amount of the light transmitted through or reflected by the detection target in the biodisc;
    determining the concentration of the detection target based on the measuring of the amount of the light transmitted through or reflected by the detection target; and
    moving a camera module, which measures the amount of the light transmitted through or reflected by the detection target in the biodisc, in a diametral direction of the biodisc.

10. The system of claim 1, the first feeding system further comprising:
    a first mechanism configured to fix the camera module.

11. The system of claim 10, the first feeding system further comprising:
    a first supporting unit configured to be connected to the first feeding motor and the first mechanism.

12. A system for measuring a concentration of a detection target using the transmission of light, the system comprising:
    an illumination unit disposed over a biodisc and configured to apply light to the detection target included in the biodisc;
    a camera module disposed below the biodisc and configured to measure an amount of the light applied by the illumination unit that is transmitted through the detection target;
    a concentration determining unit configured to determine the concentration of the detection target based on the measured amount of the light transmitted through the detection target; and
    a second feeding system having a second feeding motor to move the illumination unit in a diametral direction of the biodisc and to move separately from the camera module.

13. The system of claim 12, the second feeding system further comprising:
    a second mechanism configured to fix the illumination unit.

14. The system of claim 12, the second feeding system further comprising:
    a second supporting unit configured to be connected to the second feeding motor and the second mechanism.

* * * * *

UNITED STATES PATENT AND TRADEMARK OFFICE
CERTIFICATE OF CORRECTION

PATENT NO. : 8,852,859 B2  
APPLICATION NO. : 12/720100  
DATED : October 7, 2014  
INVENTOR(S) : Su-bong Bae et al.

Page 1 of 1

It is certified that error appears in the above-identified patent and that said Letters Patent is hereby corrected as shown below:

In the Claims

Column 10, line 17, in Claim 8, delete "diamentral" and insert -- diametral --, therefor.

Signed and Sealed this  
Fifth Day of May, 2015

Michelle K. Lee  
*Director of the United States Patent and Trademark Office*